US010064840B2

(12) United States Patent
Vishwakarma et al.

(10) Patent No.: US 10,064,840 B2
(45) Date of Patent: Sep. 4, 2018

(54) PHARMACEUTICAL COMPOSITION FOR THE TREATMENT OF MULTI-DRUG RESISTANT INFECTIONS

(71) Applicant: Council of Scientific & Industrial Research, New Delhi (IN)

(72) Inventors: Ram Vishwakarma, Jammu (IN); Ajay Kumar, Jammu (IN); Inshad Ali Khan, Jammu (IN); Sandip Bibishan Bharate, Jammu (IN); Prashant Joshi, Jammu (IN); Samsher Singh, Jammu (IN); Naresh Satti, Jammu (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/509,183

(22) PCT Filed: Oct. 21, 2015

(86) PCT No.: PCT/IN2015/050143
§ 371 (c)(1),
(2) Date: Mar. 6, 2017

(87) PCT Pub. No.: WO2016/067309
PCT Pub. Date: May 6, 2016

(65) Prior Publication Data
US 2017/0273939 A1 Sep. 28, 2017

(30) Foreign Application Priority Data
Oct. 29, 2014 (IN) .......................... 3077/DEL/2014

(51) Int. Cl.
A61K 31/352 (2006.01)
A61K 36/185 (2006.01)
A61K 31/496 (2006.01)
A61K 31/351 (2006.01)
A61K 31/7048 (2006.01)

(52) U.S. Cl.
CPC .......... A61K 31/352 (2013.01); A61K 31/351 (2013.01); A61K 31/496 (2013.01); A61K 31/7048 (2013.01); A61K 36/185 (2013.01)

(58) Field of Classification Search
CPC .................................................. A61K 31/352
See application file for complete search history.

(56) References Cited

U.S. PATENT DOCUMENTS

2010/0120902 A1   5/2010   Katiyar et al.

FOREIGN PATENT DOCUMENTS

EP        2 139 504         1/2010
IN        2009 DN 06804     6/2010
WO        WO 2008/117230 A1 10/2008
WO        WO 2009/110002 A1 9/2009

OTHER PUBLICATIONS

Astolfi, et al. 2017 "Pharmacophore-based repositioning of approved drugs as novel *S. aureus* NorA efflux pump inhibitors" *Journal of Medicinal Chemistry*. in 12 pages.
Bairwa, et al. 2012 "Rotenoids from *Boerhaavia diffusa* as Potential Anti-inflammatory Agents" *Journal of Natural Products*: in 6 pages.
Fontaine, et al. 2014 "First Identification of Boronic Species as Novel Potential Inhibitors of the *Staphylococcus aureus* NorA Efflux Pump" *Journal of Medicinal Chemistry* 57: 2536-2548.
Kalia, et al. 2012 "Capsaicin, a novel inhibitor of the NorA efflux pump, reduces the intracellular invasion of *Staphylococcus aureus*" *Journal of Antimicrobial Chemotherapy* in 8 pages.
Manu, et al. 2009 "Punarnavine Induces Apoptosis in B16F-10 Melanoma Cells by Inhibiting NF-κβ Signaling" *Asian Pacific Journal of Cancer Prevention* 10: 1031-1038.
Manu, et al. 2009 "Immunomodulatory activities of Punarnavine, an alkaloid from *Boerhaavia diffusa*" *Immunopharmacology and Immunotoxicology* 31(3): 377-387.
Mirza, et al. 2011 "Piperine as an inhibitor of the MdeA efflux pump of *Staphylococcus aureus*" *Journal of Medical Microbiology* 60: 1472-1478.
Nampoothiri, et al. 2011 "In vitro antioxidant and inhibitory potential of *Terminalia bellerica* and *Emblica officinalis* fruits against LDL oxidation and key enzymes linked to type 2 diabetes" *Food and Chemical Toxicology* 49: 125-131.
Olaleye, et al. 2010 "Antioxidant activity and hepatoprotective property of leaf extracts of *Boerhaavia diffuse* Linn against acetaminophen-induced liver damage in rats" *Food and Chemical Toxicology* 48: 2200-2205.
Prathapan, et al. 2013 "*Boerhaavia diffusa* L. attenuates angiotensin II-induced hypertrophy in H9c2 cardiac myoblast cells via modulating oxidative stress and down-regulating NF-κβ and transforming growth factor β" *British Journal of Nutrition* 110: 1201-1210.

(Continued)

*Primary Examiner* — James D. Anderson
(74) *Attorney, Agent, or Firm* — Knobbe, Martens, Olson & Bear, LLP

(57) ABSTRACT

A pharmaceutical composition for the treatment of multi-drug resistant infections includes an antimicrobial agent in combination the benzopyrano[3,4-b][1]benzopyran-12(6H)-one class of compound boeravinone B of Formula 1:

Formula 1

The bio-efficacy of anti-infective drugs can be potentiated, when used in combination with boeravinone B. Boeravinone B can overcome the resistance or multi-drug resistance developed by bacteria against quinolone, mupirocin and macrolide class of anti-bacterial agents via inhibition of bacterial efflux pumps. Thus, the compositions can be used to treat or prevent drug-resistant bacterial diseases.

12 Claims, 2 Drawing Sheets

(56) References Cited

OTHER PUBLICATIONS

Sohni, et al. 1995 "The antiamoebic effect of a crude drug formulation of herbal extracts against *Entamoeba histolytica* in vitro and in vivo" *Journal of Ethnopharmacology* 45: 43-52.

Sreeja, et al. 2009 "An in vitro study on antiproliferative and antiestrogenic effects of *Boerhaavia diffusa* L. extracts" *Journal of Ethnopharmacology* 126: 221.225.

Vineetha, et al. 2012 "Arsenic Trioxide Toxicity in H9c2 Myoblasts—Damage to Cell Organelles and Possible Amelioration with *Boerhavia diffuse*" *Cardiovasc Toxicol*: in 15 pages.

Ahmed-Belkacem, et al. 2007 "Nonprenylated rotenoids, a new class of potent breast cancer resistance protein inhibitors" *Journal of Medicinal Chemistry* 50(8): 1933-1938.

Askoura, et al. 2011 "Efflux pump inhibitors (EPIs) as new antimicrobial agents against *Pseudomonas aeruginosa*" *The Libyan Journal of Medicine* 6: 1-8.

Bhope, et al. 2011 "Rapid microwave-assisted extraction and HPTLC-Photodensitometric method for the quality assessment of *Boerhaavia diffuse* L." *Journal of AOAC International* 94(3): 795-802.

Mahamoud, et al. 2007 "Antibiotic efflux pumps in gram-negative bacteria: the inhibitor response strategy" *Journal of Antimicrobial Chemotherapy* 59: 1223-1229.

McDonnell, et al. 1999 "Antiseptics and disinfectants: Activity, Action, and Resistance" *Clinical Microbiology Reviews* 12(1): 147-179.

Olukoya, et al. 1993 "Antibacterial activity of some medicinal plants from Nigeria" *Journal of Ethnopharmacology* 39(1): 69-72.

(A)

(B)

PHARMACEUTICAL COMPOSITION FOR THE TREATMENT OF MULTI-DRUG RESISTANT INFECTIONS

FIELD OF THE INVENTION

The present invention relates to a pharmaceutical composition for the treatment of multi-drug resistant infectious diseases via potentiation of bio-efficacy of antimicrobial agents. The present invention further relates to the pharmaceutical composition having 6,9,11-trihydroxy-10-methyl[1]benzopyrano[3,4-b][1]benzopyran-12(6H)-one (boeravinone B) to overcome the resistance or multi-drug resistance developed by bacteria against quinolone, mupirocin and macrolide class of antibacterial. The present invention also relates to the method of treating a bacterial infection in a subject, by co-administering an antimicrobial agent and compounds boeravinone B in such a manner as to achieve an bio enhancement in efficacy of the anti-microbial agent due to effective efflux pump inhibitory activity of the compound of the invention at a site of infection.

BACKGROUND OF THE INVENTION

The problem of resistance to a large variety of anti-infective agents by bacterial and fungal pathogens indicates warning sign to infection combating strategies. The defiant nature of these pathogens were mostly associated with the higher extrusion rate of anti-infective agents by transmembrane efflux pumps like NorA (*Staphylococcus aureus*) to quinolone class of antibacterials like norfloxacin and ciprofloxacin, 1258c (*Mycobacterium tuberculosis*) to rifampicin, Mde A (*S. aureus* Mup$^r$-1) to mupirocin, Tet K (*S. aureus* SA-K2192) to tetracyclin, and Msr A (*S. aureus* SA-K2191) efflux pump to erythromycin. Therefore, use of suitable efflux pump inhibitor in combination with resistance-susceptible antibacterials in resistant pathogens would re-establish their sensitivity to the same. Large number of synthetic (acrylic acid amides, boronate species and 2-phenyl quinolones) and natural products (piperine and capsaicin) are known to have bacterial efflux pump inhibition properties. Furthermore, these compounds are reported to potentiate the bioefficacy of known drugs by reducing multi-drug resistance via their ability to inhibit efflux pumps (WO 2009/110002 A1, Fontaine, F. et al, *J. Med. Chem.* 2014, 57, 2536; Sabatini, S. et. al., *J. Med. Chem.* 2013, 56, 4975; Mirza, Z. M. et. al. *J. Med. Microbiol.* 2010, 60, 1472; Kalia, N. P. et al., *J. Antimicrob. Chemother.* 2012, 67, 2401).

Rotenoids are naturally occurring substances containing a cis-fused tetrahydrochromeno[3,4-b]chromene nucleus. Rotenoids are related to the isoflavones. Boeravinone B (6,9,11-trihydroxy-10-methyl[1]benzopyrano[3,4-b][1]benzopyran-12(6H)-one) is a rotenoid class of compound isolated from traditional Indian medicinal plant *Boerhavia diffusa* Linn (Punernava). In Ayurveda, *Boerhavia diffusa* is reported to posseess wide variety of medicinal properties including its anti-aging effects. Beside this, the root extract of the *Boerhavia diffusa* posses antioxidant, hepatoprotective (Olaleye M. T. et al, *Food Chem. Tox.* 2010, 48, 2200-2205, Prathapan A. et al., *J. Food Biochem.* 2011, 35, 1548-1554) and cardioprotective properties (Vineetha V. P et al., *Cardiovas. Tox.* 2013, 13, 123-137; Prathapan A. et al., *Br. J. Nutr.* 2013, 110, 1201-1210). Compounds isolated from this plant includes alkaloid punernavine which is known to possess various pharmacological activities such as anticancer (Manu K. A et al., *Asian Pac. J. Can. Prev.* 2009, 10, 1031-1037), antiestrogenic (Sreeja S. et al., *J. Ethnopharmacol.*, 2009, 126, 221-225), immunomodulatory (Manu K. A. et al., *Immunopharmacol Immunotoxicol.* 2009, 31, 377-387) and antiamoebic activity (Sohni Y. R., et al., *J. Ethnopharmacol.* 1995, 45, 43-52). Boeravinone A-J are reported to posses anti-inflammatory (WO 2008117230; EP 2139504; IN 2009DN06804; US 20100120902; Bairwa K. et al., *J. Nat. Prod.*, 2013, 76, 1393-1398) and breast cancer resistant protein (BCRP) inhibitory activity (Ahmed-Belkacem A. et al., *J. Med. Chem.*, 2007, 50, 1933-1938). In the present invention, we report the new use of 6,9,11-trihydroxy-10-methyl[1]benzopyrano[3,4-b][1]benzopyran-12(6H)-one for potentiating the bioefficacy of known antimicrobial drugs via inhibition of bacterial efflux pump(s).

OBJECTIVES OF THE INVENTION

The main object of the present invention is to provide a pharmaceutical composition comprising benzopyrano[3,4-b][1]benzopyran-12(6H)-one class of compound, 6,9,11-trihydroxy-10-methyl[1]benzopyrano[3,4-b][1]benzopyran-12(6H)-one (boeravinone B) of formula 1

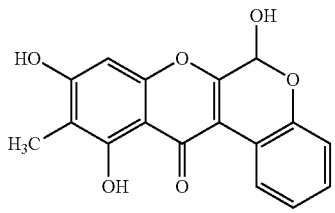

Formula 1 isolated from the plant *Boerhavia diffusa* Linn with antimicrobial agents.

Another object of the present invention is to provide 6,9,11-trihydroxy-10-methyl[1]benzopyrano[3,4-b][1]benzopyran-12(6H)-one (boeravinone B) for potentiating the bio efficacy of antimicrobial drugs via inhibition of their respective bacterial efflux pumps.

Still another objective of the present invention is to provide new multi-drug resistance reversal agent for quinolone, mupirocin and macrolide class of anti-bacterials in multidrug resistant bacterial infections.

Still another objective of the invention is to provide novel treatment for drug-resistant or multi-drug resistant bacterial diseases in combination with quinolone, mupirocin or macrolide class of antibacterial.

SUMMARY OF THE INVENTION

Accordingly, present invention provides a pharmaceutical composition for potentiating bio-efficacy of drugs for the treatment of multi-drug resistance wherein the composition comprises boeravinone B of formula 1 in combination with an effective amount of antimicrobial agents, along with pharmaceutically acceptable carrier wherein formula 1 is

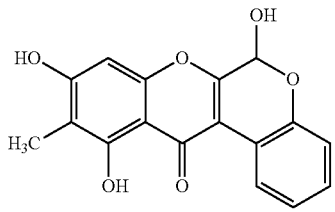

Formula 1

In second embodiment of the invention wherein the dose of compound of formula 1, 6,9,11-trihydroxy-10-methyl[1]benzopyrano[3,4-b][1]benzopyran-12(6H)-one with suitable anti-infective agents in the ratio of 1:99 to 99:1 to overcome the multi-drug resistance developed by bacteria against quinolone, mupirocin and macrolide class of anti-infective agents.
   a. wherein, quinolone class of antibacterials comprises cinoxacin, nalidixic acid, oxolinic acid piromidic acid, pipemidic acid, rosoxacin (first-generation); ciprofloxacin, enoxacin, fleroxacin, lomefloxacin, nadifloxacin, norfloxacin, ofloxacin, pefloxacin, rufloxacin (second-generation); balofloxacin, grepafloxacin, levofloxacin, pazufloxacin, sparfloxacin, temafloxacin, tosufloxacin (third-generation); or clinafloxacin, gatifloxacin, gemifoxacin, moxiloxacin, sitafloxacin, trovafloxacin, prulifloxacin, delafloxacin, JNJ-Q2, and nemonoxacin (fourth-generation) and their salts,
   b. mupirocin
   c. macrolide class of antibacterials comprises azithromycin, dirithromycin, erythromycin, roxithromycin, telithromycin, carbomycin A, josamycin, kitasamycin, midecamycin, oleandomycin, solithromycin, spiramycin, troleandomycin, tylosin/tylocine, telithromycin, cethromycin, solithromycin, spiramycin, ansamycin, oleandomycin, carbomycin and their salts.

In another embodiment of the invention, a pharmaceutical composition, wherein, the combination of the compound formula 1 leads to enhancement in antibacterial activity of ciprofloxacin, mupirocin and erythromycin with $MEC_4$ values ($MEC_4$=Minimum effective concentration of boeravinone B that brings about 4 fold reduction in the MIC) of 12.5, 25 and 25 µM, respectively in Multi drug resistance infections.

In another embodiment of the invention, a pharmaceutical composition, wherein, the combination of the compound of formula 1 with ciprofloxacin, mupirocin and erythromycin leads to enhancement in antibacterial activity of ciprofloxacin, mupirocin and erythromycin by 8, 4 and 4 folds respectively in Multi drug resistance infections.

In another embodiment of the invention, a pharmaceutical composition wherein, the multi-drug resistance developed in the bacteria is selected from the group consisting of *Staphylococcus aureus, Pseudomonas aeruginosa, Pseudomonas fluor escens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter fi-eundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemopliilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides S452A homology group, Bacteroides vulgatus, Bacteroides ovalus, Bacteroides thetaiotaomicron, Bacteroides uniformis, Bacteroides eggerthii,* and *Bacteroides splanclmicus.*

In one more embodiment of the invention, the compound boeravinone B of pharmaceutical composition is isolated from *Boerhavia diffusa* Linn.

In another embodiment of the invention, a method is presented for treating or preventing infectious diseases by identifying a patient suffering or at a risk of developing a infection by administering the composition of quinolone, mupirocin and macrolide class of antibacterial agents with the compound of formula 1, at therapeutically-effective dose.

In still another embodiment of the invention, a pharmaceutical composition wherein the pharmaceutically acceptable excipient is selected from a group consisting of saccharides (such aslactose, starch, dextrose), stearates (such as stearic acid, magnesium stearate), polyvinyl pyrrolidine, dicalcium phosphate dihydrate, eudragit polymers, celluloses, polyethylene glycol, polysorbate 80, sodium lauryl sulfate, magnesium oxide, silicon dioxide, carbonates (such as sodium carbonate, sodium bicarbonate), talc.

In another embodiment of the invention wherein the above described compound is useful to overcome the multi-drug resistance associated with quinolone, mupirocin and macrolide class of anti-bacterials.

LIST OF ABBREVIATIONS

ANOVA: Analysis of variance; CFU: Colony forming unit; MDR: Multi-drug resistance; $MEC_4$: Minimum effective concentration required for equal sensitivity of antibacterial agent in both wild and resistant cells; MIC: minimum inhibitory concentration; *S. aureus: Staphylococcus aureus.*

DETAILED DESCRIPTION OF THE INVENTION

The present invention reports benzopyrano[3,4-b][1]benzopyran-12(6H)-one class of compound boeravinone B of formula 1 as bio efficacy enhancer of known antimicrobial agents via inhibition of their efflux pump in multi drug resistant bacteria.

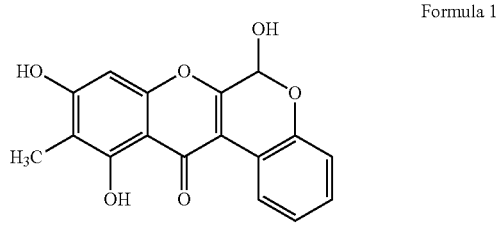 [SMILES: Cc1c(O)cc2oc3c(c(=O)c2c1O)-c1ccccc1OC3O]

Formula 1

Boeravinone B (formula 1) displayed inhibition of various bacterial efflux pumps (Nor A, Mde A and Msr A), which are responsible for development of multi-drug resistance to respective substrate antibacterial drug ciprofloxacin, mupirocin and erythromycin. Boeravinone B displayed promising inhibitory activity against Nor A (*Staphylococcus aureus*) efflux pump, as evidenced by enhanced antibacterial activity of ciprofloxacin ($MEC_4$ 12.5 µM) (Table 1) when used in combination. Boeravinone B also augmented antibacterial activity of mupirocin and erythromycin with $MEC_4$ value of 25 µM, via inhibition of *S. aureus* Mde A (Table 2) and Msr A efflux pumps (Table 3), respectively when used in combination.

Figure 1:
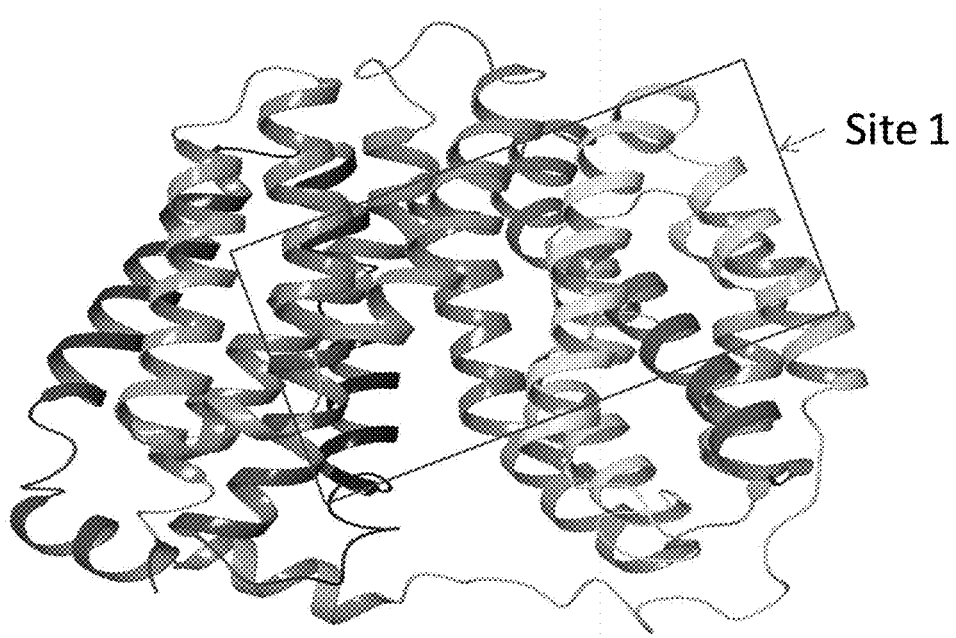
FIG. 1. is a diagram illustrating the Nor-A binding interactions of compound of formula 1 (boeravinone B). (A) Nor A efflux pump with site 1. (B) Nor A binding interactions of boeravinone B at site 1.
Figure 1:
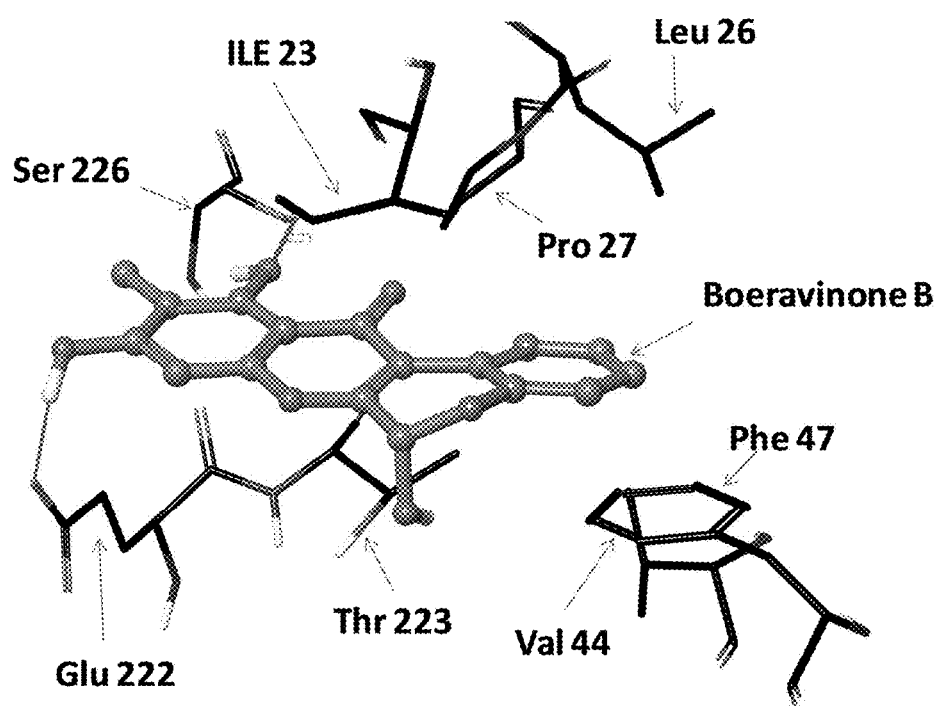

The molecular modeling studies with bacterial Nor A efflux pump homology model revealed that boeravinone B binds to the Ile23 and Glu222 residue of efflux pump by strong H-bonding formed by phenolic hydroxyl groups as shown in FIG. 1. The potent efflux pump inhibitory activity of boeravinone B clearly indicate its potential to develop as a part of combination in anti-infective therapy for the treatment of resistance or multidrug resistance.

As used herein, the terms below have the meanings indicated.

The phrase therapeutically effective is intended to qualify the amount of active ingredients used in the treatment of a disease or disorder. This amount will achieve the goal of reducing or eliminating the disease or disorder.

As used herein, reference to treatment of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

The phrase infectious diseases is used to define the abnormal diseased state of host organism caused by the gram-negative or gram-positive bacteria including *Staphylococcus aureus, Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter fieundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemopliilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* S452A homology group, *Bacteroides vulgatus, Bacteroides ovalus, Bacteroides thetaiotaomicron, Bacteroides uniformis, Bacteroides eggerthii,* and *Bacteroides splanclmicus.*

The phrase drug-resistance is used to define the lower sensitivity or lower efficacy of the well known chemotherapeutic agent to microorganism due to higher rate of extrusion of respective substrate drug by the efflux pump.

The phrase multi-drug resistance is used to define the lower sensitivity or lower efficacy of the well known chemotherapeutic agents to microorganism due to higher rate of extrusion of substrate drugs by the efflux pump.

Quinolone class of antibacterials comprises cinoxacin, nalidixic acid, oxolinic acid piromidic acid, pipemidic acid, rosoxacin (first-generation); ciprofloxacin, enoxacin, fleroxacin, lomefloxacin, nadifloxacin, norfloxacin, ofloxacin, pefloxacin, rufloxacin (second-generation); balofloxacin, grepafloxacin, levofloxacin, pazufloxacin, sparfloxacin, temafloxacin, tosufloxacin (third-generation); or clinafloxacin, gatifloxacin, gemifoxacin, moxiloxacin, sitafloxacin, trovafloxacin, prulifloxacin, delafloxacin, JNJ-Q2, and nemonoxacin (fourth-generation) and their salts.

Macrolide class of antibacterials comprises azithromycin, dirithromycin, erythromycin, roxithromycin, telithromycin, carbomycin A, josamycin, kitasamycin, midecamycin, oleandomycin, solithromycin, spiramycin, troleandomycin, tylosin/tylocine, telithromycin, cethromycin, solithromycin, spiramycin, ansamycin, oleandomycin, carbomycin and their salts.

The compounds of the invention can be used to treat a patient (e.g. a human) that suffers from or is at a risk of suffering from a disease, disorder, condition, or symptom described herein. The compounds of the present invention can be used in combination with other suitable antimicrobial agents. The present invention describe the methods of treating or preventing infectious disorders caused by the bacteria using compound of formula I in combination with suitable antimicrobial agents. Each such treatment described above includes the step of administering to a patient in need thereof a therapeutically effective amount of the compound of the invention described herein to delay, reduce or prevent such a disease, disorder, condition, or symptom.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Following examples are given by way of illustration and should not construed the scope of present invention.

Example 1. Isolation of Boeravinone B from Roots of *Boerhavia Diffusa*

*Boerhavia diffusa* plant material was collected from the Jammu region of India and dried under shadow. Whole plant material specimen (Voucher Specimen No. 21713) was deposited in Janaki Ammal Herbarium of Indian Institute of Integrative Medicine, Jammu Root of this plant were separated and powdered. The 500 gms powdered material was extracted with dichloromethane: Methanol mixture (1:1 ratio) (3 L×2) using cold maceration method. Solvent was evaporated on vacuo rotavapor and crude extract was subjected to silica gel column chromatography using Dichloromethane:Methanol (95:5 ratio). Structure of boeravinone B was characterized by comparison of spectral data with literature values.

Example 2. Inhibition of Nor A Bacterial Efflux Pump of *Staphylococcus aureus* by Boeravinone B Combination studies were performed by a broth checkerboard method A series of twofold dilutions of test ciprofloxacin in Muller Hinton Broth (pH 7.0) was tested in combination with twofold dilutions of boeravinone B in 96-well microtiter plates. The final concentrations of ciprofloxacin ranged from 0.03 mg/L/ml to 64 mg/L and for boeravinone B from 0.8 mg/L to 50 mg/L. Piperine at a same concentration range as that of boeravinone B was used as standard EPI. Nor A overexpressing derivative of a clinical isolate (SA-1199B) obtained from *S. aureus* strain ATCC No. 29213 (American Type Culture Collection Manassas, Va., USA) was kindly gifted by Dr G. W. Kaatz (Wayne State University School of Medicine, Detroit, Mich., USA). Bacterial inocula were prepared by adjusting the inoculum density of the overnight grown *Staphylococcus aureus* 1199B (Nor A overexpressing) to 0.5 McFarland (~1.5×10$^8$ CFU/mL of *Escherichia coli*). These inocula were diluted 1:100 in sterile normal saline and 100 µl of these diluted inocula was dispensed in each well. The final bacterial inoculum reached in each well was equal 5×10$^5$ CFU/mL. The plates were incubated at 37° C. for 24 hrs. The MIC was read visually as the lowest concentration of ciprofloxacin inhibiting the growth of bacteria as evident from the absence of turbidity.

TABLE 1

The Nor-A efflux pump inhibition activity of boeravinone B when used in combination with ciprofloxacin.

| Compound | MIC Ciprofloxacin (µg/ml) Alone | MIC (µg/ml) of ciprofloxacin in presence of compound Compound concentration (µM) | | | | | | | $MEC_4$ (µM) |
|---|---|---|---|---|---|---|---|---|---|
| | | 50 | 25 | 12.5 | 6.25 | 3.12 | 1.5 | 0.7 | |
| Boeravinone B | 8 | 1 | 1 | 2 | 4 | 4 | 8 | 8 | 12.5 |
| Piperine | 8 | 4 | 4 | 8 | 8 | 8 | 8 | 8 | >50 |

$MEC_4$ = Minimum effective concentration of compound that brings about 4 fold reduction in the MIC of Ciprofloxacin.

Table-1 shows that boeravinone B exhibited an $MEC_4$ value of 12.5 µM, which indicate that at 25 µM concentration it reduces MIC of mupirocin by 4 fold s. Though at highest concentration (50 µM) boeravinone B could decrease the MIC of ciprofloxacin to 8 folds (from 8 µg/ml to 1 µg/ml)

Example 3. Inhibition of Mde A Bacterial Efflux Pump of *Staphylococcus aureus* by Boeravinone B

*Staphylococcus aureus* Mupr-1 (Mde A overexpressing) was prepared in-house from SA-1199-Wild type clinical isolate which was gifted by Prof. Dr G. W. Kaatz (Wayne State University School of Medicine, Detroit, Mich., USA) by serially passaging SA-1199 strain on mupirocin. Combination studies were performed by a broth checkerboard method. A series of twofold dilutions of test mupirocin in Muller Hinton Broth (pH 7.0) was tested in combination with twofold dilutions of boeravinone B in 96-well microtiter plates. The final concentrations of mupirocin ranged from 0.03 mg/L/ml to 64 mg/L and for boeravinone B from 0.8 mg/L to 50 mg/L. Bacterial inocula were prepared by adjusting the inoculum density of the overnight grown *Staphylococcus aureus* $Mup^{r-1}$ (Mde A overexpressing) to 0.5 McFarland (~1.5×10$^8$ CFU/mL of *Escherichia coli*). Mde A overexpressing derivative *S. aureus* strain was prepared in lab upon mupirocin treatment ($Mup^r$-1) from *S. aureus* strain ATCC No. 29213 (American type culture collection Manassas, Va., USA). These inocula were diluted 1:100 in sterile normal saline and 100 µl of these diluted inocula was dispensed in each well. The final bacterial inoculum reached in each well was equal 5×10$^5$ CFU/mL. The plates were incubated at 37° C. for 24 hrs. The MIC was read visually as the lowest concentration of mupirocin inhibiting the growth of bacteria as evident from the absence of turbidity. The MIC was read visually as the lowest concentration of mupirocin inhibiting the growth of bacteria as evident from the absence of turbidity.

Table 2 shows that boeravinone B exhibited an $MEC_4$ of 25 µM, which indicate that at 25 µM concentration it reduces MIC of mupirocin by 4 fold.

Example 4. Inhibition of Msr A Bacterial Efflux Pump of *Staphylococcus aureus* Boeravinone B Combination studies were performed by a broth checkerboard method. A series of two-fold dilutions of test Erythromycin in Muller Hinton Broth (pH 7.0) was tested in combination with twofold dilutions of boeravinone B in 96-well microtiter plates. The final concentrations of erythromycin ranged from 0.03 mg/L/ml to 64 mg/L and for boeravinone B from 0.8 mg/L to 50 mg/L. MsrA overexpressing *S. aureus* derivative (RN4220) obtained by transforming with pSK265 into which the gene for MsrA has been cloned from *S. aureus* ATCC 29213 (American type culture collection Manassas, Va., USA) was kindly gifted by Dr G. W. Kaatz (Wayne State University School of Medicine, Detroit, Mich., USA). Bacterial inocula were prepared by adjusting the inoculum density of the overnight grown *Staphylococcus aureus* SA-K2191 (Msr A overexpressing) to 0.5 McFarland (~1.5×10$^8$ CFU/mL of *Escherichia coli*). These inocula were diluted 1:100 in sterile normal saline and 100 µl of these diluted inocula was dispensed in each well. The final bacterial inoculum reached in each well was equal 5×10$^5$ CFU/mL. The plates were incubated at 37° C. for 24 hrs. The MIC was read visually as the lowest concentration of erythromycin inhibiting the growth of bacteria as evident from the absence of turbidity. The MIC was read visually as the lowest concentration erythrocycin inhibiting the growth of bacteria as evident from the absence of turbidity.

TABLE 2

*S. aureus* Mde A efflux pump inhibition activity of boeravinone B when used in combination with mupirocin.

| Compound | MIC of mupirocin (µg/ml) Alone | MIC (µg/ml) of mupirocin in presence of compound Compound concentration (µM) | | | | | | | $MEC_4$ (µM) |
|---|---|---|---|---|---|---|---|---|---|
| | | 50 | 25 | 12.5 | 6.25 | 3.12 | 1.5 | 0.7 | |
| Boeravinone B | 256 | 64 | 64 | 128 | 256 | 256 | 256 | 256 | 25 |

$MEC_4$ = Minimum effective concentration of boeravinone B that brings about 4 fold reduction in the MIC of Mupirocin

TABLE 3

S. aureus Msr A efflux pump inhibition activity of boeravinone B when used in combination with erythromycin.

| Compound | MIC of Erythromycin (µg/ml) Alone | MIC (µg/ml) of Erythromycin in presence of compound Compound concentration (µM) | | | | | | | $MEC_4$ (µM) |
|---|---|---|---|---|---|---|---|---|---|
| | | 50 | 25 | 12.5 | 6.25 | 3.12 | 1.5 | 0.7 | |
| boeravinone B | 64 | 16 | 16 | 32 | 64 | 64 | 64 | 64 | 25 |

$MEC_4$ = Minimum effective concentration of boeravinone B that brings about 4 fold reduction in the MIC of erythromycin.

Table 3 shows that boeravinone B exhibited an $MEC_4$ of 25 µM, which indicate that at 25 µM concentration it reduces MIC of erythromycin by 4 folds.

Example 5. Molecular Modeling Studies with Nor A Efflux Pump

*Staphylococcus aureus* efflux pump Nor A, is a member of MFS (major facilitator superfamily) group, whose crystal structure is still not solved, but fortunately homology based prediction of its transmembrane structure and ligand binding was carried out in past. Similarly here, initial blast sequence of the nor A efflux pump of *Staphylococcus aureus* (Uniport ID: I3RSV5) was retrived from Uniprot protein knowledgebase database. Further based on homolog nucleotide sequences search glycerol-3-phosphate transporter pump was considered as template (PDB: 1PW4) for structure prediction and refinement studies using Prime. Stereo chemical quality of the final model was assessed by Ramachandran plot. Homology modeled nor A protein structure is minimized by protein preparation wizard using OPLS 20005 force field. As the exact binding site of substrate and inhibitor to Nor A efflux pump is not available, sitemap analysis was performed, in which two major binding cavities (site1 and site2) were observed in nor A protein. Site1 is surrounded by the large number of transmembrane loops and located deeper in efflux pump while site2 is quiet open and it is located on surface. Therefore, Ligand binding site was defind based on the optimization of docking protocol using XP docking score and free energy of the binding (ΔG) of ciprofloxacine, capsaicine, piperine and reserpine, where receptor vanderwaal radii, size of grid box and residue lining the cavity were varied. Optimized grid box have size of 25 A° and receptor vanderwaal radii of 1.0 A°. Further docked poses were minimized by macromodel to optimize receptor-ligand binding interactions. Optimized protocol is used for the boeravinone B docking using GLIDE software and binding affinity calculations using Prime MMGB/SA function predicted ligand-efflux pump interactions of boeravinone B with Nor A pump are shown in FIG. 1.

The molecular modeling studies with bacterial Nor A efflux pump homology model revealed that boeravinone B binds to the Ile23 and Glu222 residue of efflux pump by strong H-bonding formed by phenolic hydroxyl groups as shown in FIG. 1. The potent efflux pump inhibitory activity of boeravinone B clearly indicate its potential to develop as a part of combination in anti-infective therapy for the treatment of resistance or multidrug resistance.

ADVANTAGES OF THE INVENTION

The main advantages of the present invention are:
Boeravinone B showed inhibition of bacterial efflux pump inhibition activity.
Boeravinone B showed potentiation of bio-efficacy of ciprofloxacin, mupirocin and erythromycin by 8, 4 and 4 folds respectively in MDR *S. aureus* bacteria.
Boeravinone B displayed promising Nor A, efflux pump inhibition activity than reference natural product piperine.
Compounds of the invention are stable.

We claim:
1. A pharmaceutical composition for potentiating bio-efficacy of drugs for the treatment of bacterial multi-drug resistance infections wherein the composition comprises boeravinone B of formula 1,

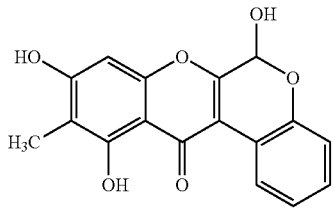

Formula 1 in combination with an effective amount of an antibacterial agent, along with a pharmaceutically acceptable carrier.
2. A pharmaceutical composition as claimed in claim 1, wherein the ratio of the boeravinone B of formula 1 to the antibacterial agent is 1:99 to 99:1 by weight.
3. A pharmaceutical composition as claimed in claim 1, wherein the pharmaceutically acceptable carrier is selected from the group consisting of a saccharide, a stearate, polyvinyl pyrrolidine, dicalcium phosphate dihydrate, eudragit polymers, celluloses, polyethylene glycol, polysorbate 80, sodium lauryl sulfate, magnesium oxide, silicon dioxide, a carbonate and talc.
4. A method of treating a multi-drug resistant bacterial infection in a subject comprising administering the composition according to claim 1 to a subject infected with a multi-drug resistant bacteria.
5. The method according to claim 4, wherein the composition overcomes multi-drug resistance developed by bacteria against a quinolone class of antibacterials, mupirocin and/or a macrolide class of antibacterial agents,
wherein, the quinolone class of antibacterials comprises:
(a) a first generation quinolone selected from the group consisting of cinoxacin, nalidixic acid, oxolinic acid, piromidic acid, pipemidic acid, rosoxacin and a salt thereof; (b) a second generation quinolone selected from the group consisting of ciprofloxacin, enoxacin, fleroxacin, lomefloxacin, nadifloxacin, norfloxacin, ofloxacin, pefloxacin, rufloxacin and a salt thereof; (c) a third generation quinolone selected from the group consisting of balofloxacin, grepafloxacin, levofloxacin, pazufloxacin, sparfloxacin, temafloxacin, tosufloxacin and a salt thereof; or (d) a fourth generation quinolone selected from the group consisting of clinafloxacin, gatifloxacin, gemifoxacin, moxiloxacin, sitafloxacin, trovafloxacin, prulifloxacin, delafloxacin, JNJ-Q2, nemonoxacin and a salt thereof, and wherein the macrolide class of antibacterials comprises azithromycin, dirithromycin, erythromycin, roxithromycin, telithromycin, carbomycin A, josamycin, kitasamycin, midecamycin, oleandomycin, solithromycin, spiramycin, troleandomycin, tylosin/tylocine, telithromycin, cethromycin, solithromycin, spiramycin, ansamycin, oleandomycin, carbomycin or a salt thereof.

6. The method according to claim 4, wherein the antibacterial agent is ciprofloxacin, mupirocin or erythromycin, and wherein the combination of the boeravinone B of formula 1 and the antibacterial agent leads to enhancement in antibacterial activity of the ciprofloxacin, mupirocin or erythromycin with MEC4 values (MEC4=Minimum effective concentration of boeravinone B that brings about 4 fold reduction in the MIC) of 12.5, 25 and 25 µM, respectively in multi drug resistant infections.

7. The method as claimed in claim 4, wherein the antibacterial agent is ciprofloxacin, mupirocin or erythromycin, and wherein the combination of the boeravinone B of formula 1 and the antibacterial agent leads to enhancement in antibacterial activity of the ciprofloxacin, mupirocin or erythromycin by 8-, 4- and 4-fold, respectively, in multi drug resistant infections.

8. The method as claimed in claim 4 wherein the bacteria is selected from the group consisting of *Staphylococcus aureus, Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratiama rcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides vulgatus, Bacteroides ovalus, Bacteroides thetaiotaomicron, Bacteroides uniformis, Bacteroides eggerthii,* and *Bacteroides splanchnicus.*

9. The method according to claim 4, wherein the composition overcomes multidrug resistance due to inhibition of efflux pump(s).

10. The pharmaceutical composition according to claim 3, wherein the saccharide is selected from the group consisting of lactose, starch and dextrose.

11. The pharmaceutical composition according to claim 3, wherein the stearate is selected from the group consisting of stearic acid and magnesium stearate.

12. The pharmaceutical composition according to claim 3, wherein the carbonate is selected from the group consisting of sodium carbonate and sodium bicarbonate.

\* \* \* \* \*